United States Patent [19]

Garber et al.

[11] 4,215,568
[45] Aug. 5, 1980

[54] RAPID WATER ACTIVITY DETERMINING DEVICE AND METHOD

[75] Inventors: Esther B. Garber, Brookline; Lloyd Cox, Natick, both of Mass.

[73] Assignee: The United States of America as represented by the Secretary of the Army, Washington, D.C.

[21] Appl. No.: 44,125

[22] Filed: May 31, 1979

[51] Int. Cl.³ ............................................. G01N 25/56
[52] U.S. Cl. ...................................... 73/73; 73/17 A; 73/29; 73/336
[58] Field of Search ..................... 73/17 A, 29, 336, 73

[56] References Cited

U.S. PATENT DOCUMENTS

| 2,662,393 | 12/1953 | Rzasa | 73/17 A |
| 2,777,324 | 1/1957 | Ives | 73/73 |

Primary Examiner—Donald O. Woodiel
Attorney, Agent, or Firm—Nathan Edelberg; Robert P. Gibson; Lawrence E. Labadini

[57] ABSTRACT

Apparatus and method for determining the water activity (Aw) of a water-containing composition, such as a food, within approximately 10 minutes, by rapidly establishing equilibrium between the water-containing composition and the atmosphere with which it is in contact while maintaining the temperature substantially constant and determining the dew point of this atmosphere, from which the water activity is calculable from the ratio of the partial water vapor pressure at the dew point to the vapor pressure of pure water at the temperature of the atmosphere with which the water-containing composition is in equilibrium.

10 Claims, 1 Drawing Figure

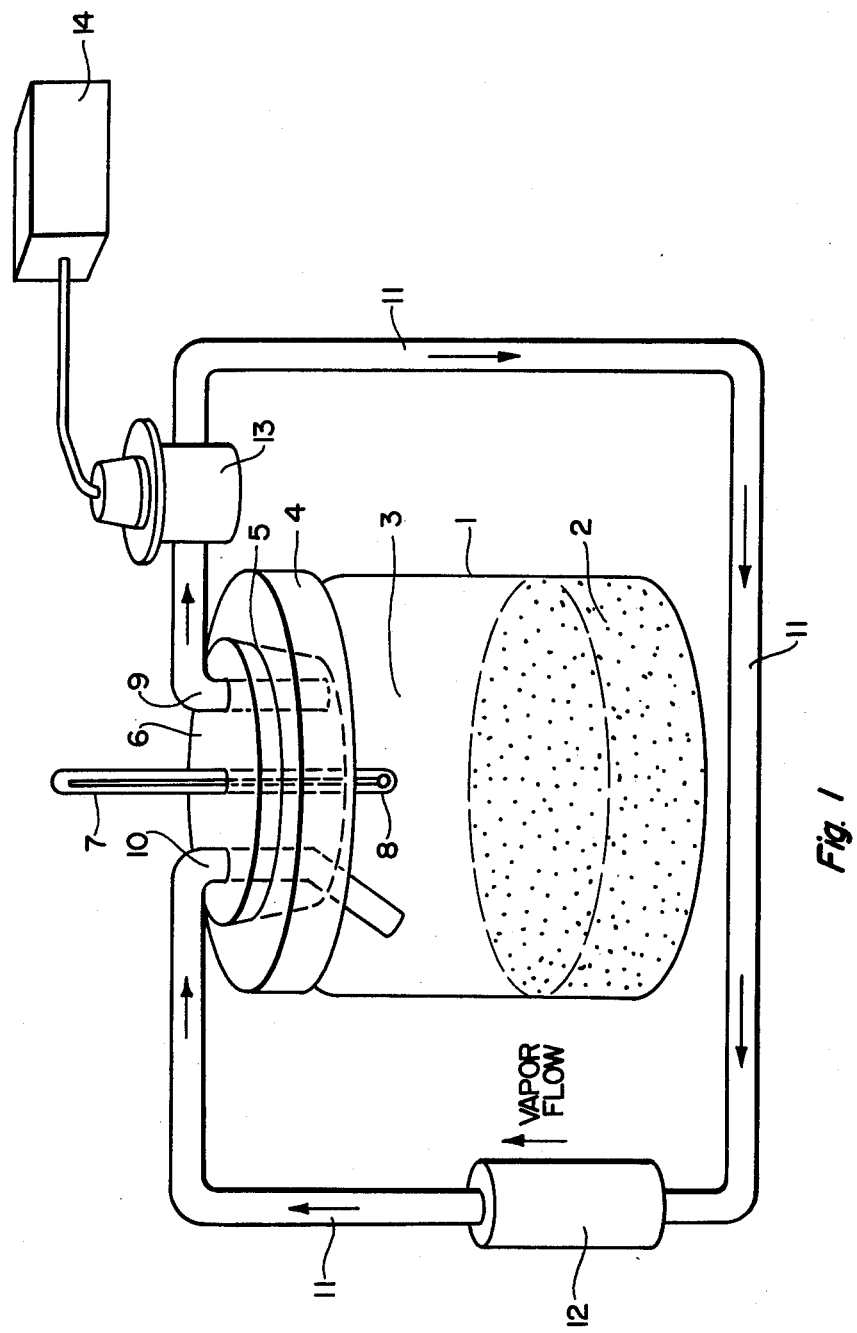

RAPID WATER ACTIVITY DETERMINING DEVICE AND METHOD

The invention described herein may be manufactured, used, and licensed by or for the Government for governmental purposes without the payment to us of any royalty thereon.

BACKGROUND OF THE INVENTION

This invention relates to an apparatus and method for determining the water activity of a water-containing composition within approximately 10 minutes. More particularly, the invention relates to an apparatus and method for rapidly and accurately determining the water activity of a food.

Water activity is a convenient and effective way of expressing how much free (unbound) water exists in a water-containing composition. Water activity is a very important characteristic of many, if not most, foods since it, together with the temperature of a food, determines the susceptibility of the food to growth of bacteria and fungi therein. This is an important consideration for human beings since health and safety are greatly dependent on the control of bacterial and fungal growth in foods, while the enjoyment of certain foods is conditioned by the degree of proliferation of certain beneficial or desirable micro-organisms therein.

An object of the present invention, therefore, is to provide an apparatus and method for rapidly determining the water activity of a water-containing composition, such as a food.

Other objects and advantages of the invention will be apparent from the following description when taken in connection with the accompanying drawing.

DESCRIPTION OF PREFERRED EMBODIMENT

The apparatus of the invention is illustrated in the drawing, wherein

FIG. 1 is a vertical plan view, partially in perspective, of a water activity determining apparatus in accordance with the invention.

Referring to the drawing more specifically, reference numeral 1 designates a sample container in which is placed a quantity of sample 2, for example a food, which is preferably subdivided so as to accomplish rapid equilibration of the moisture in the sample with the atmosphere 3 over the sample. The sample container is provided with a screw-on cap 4 and gasket of the Oster blender type having a center opening 5 which is approximately 2.5 cm. in diameter. In center opening 5 there is inserted securely a three-holed rubber stopper 6. Approximately $6.35 \times 10^{-3}$ m o.d. hollow tubes, preferably glass, are inserted through two of the stopper holes to connect with the atmosphere 3 over the sample. A precision thermometer 7, or other temperature-measuring device, is inserted through the third hole in the rubber stopper so that the bulb 8 of the thermometer will be bathed by the atmosphere 3 in the sample container and will be in close proximity to the water-containing composition. One of the hollow tubes serves as an exit tube 9 for the atmosphere 3, while the other of the hollow tubes serves as an entry tube 10, bent to direct the flow of atmosphere to the wall of sample container 1, for the atmosphere being returned to the sample container after being circulated outside of the sample container through conduit 11 at a rate of from about $1.26 \times 10^{-5}$ m³/s to about $2.36 \times 10^{-5}$ m³/s under impulses imparted thereto by a diaphragm pump 12, such as a Borman-Rupp pump. Conduit 11 is preferably made of "Tygon" tubing. The arrows within conduit 11 indicate the direction of flow of atmosphere 3. Shortly after exiting from the sample container through exit tube 9 the atmosphere 3 is passed through a sensor 13 which is designed to measure dew point temperature with a thermo-electric dew point hygrometer 14, for example, a Model 880 Dew Point Hygrometer manufactured by EG&G International, Inc., Environmental Equipment Division, 151 Bear Hill Road, Waltham, Mass. 02154. Instruction Manual TM71-174 is available from the manufacturer. The atmosphere containing water vapor passes through the sensor, then through conduit 11 to the diaphragm pump 12, then through conduit 11 back into the sample container via entry tube 10 to complete the cycle and thus bring about equilibration of the moisture in the atmosphere 3 with the moisture in the sample 2 after sufficient circulation of atmosphere 3 through the system.

The ambient temperature of the atmosphere is read on the thermometer 7 when it attains a constant value. The purpose of the sensor is to sense the attainment of the equilibrium dew point of the atmosphere 3. The temperature at which the equilibrium dew point is attained is indicated on the dew point meter of the Model 880 Dew Point Hygrometer of the EG&G International, Inc.

In explanation of the construction and principle of operation of the thermoelectric dew point hygrometer, more particularly the Model 880 Dew Point Hygrometer with its sensor 13, a cooled metal surface within the sensor is contacted by the gaseous atmosphere forced out of the sample container by the operation of the diaphragm pump so that the gas at the metal surface is at the temperature of the metal surface. When the temperature of the metal surface is cooled to or below the dew point of the gaseous atmosphere, condensation of moisture on the metal surface occurs and water in the form of droplets (or ice crystals if the temperature is low enough) will form thereon. If the metal surface is maintained below the dew point (however slight this temperature difference may be) condensation will continue and result in an increasing amount of water on the metal surface. If the metal surface is at a temperature above the dew point temperature, the water will begin to evaporate from the metal surface, resulting in a reduction in the amount of water on the metal surface. Only when the metal surface temperature is exactly at the dew point will a state of dynamic equilibrium exist, i.e., where the rate at which molecules of water leaving the metal surface is equal to the rate at which water molecules condense on the metal surface from the surrounding gaseous atmosphere. Thus, the amount of water on the metal surface is unchanging at the dew point.

The metal surface within the sensor which carries out the above-described function is a gold plated copper disc about $6.35 \times 10^{-3}$ m in diameter with a highly polished, mirror-like surface. The temperature of the metal surface is measured by means of a precision thermistor embedded in the metal surface, which forms a part of an electrical bridge circuit. This circuit is designed to linearize the thermistor characteristic so that the output thereof is displayed as degrees Centigrade or Fahrenheit on the front panel of the dew point hygrometer.

The presence of condensate on the mirror surface is detected by means of an optical system in which light from a neon lamp in the sensor is directed to the mirror surface where it is reflected at an angle to intersect a photoconductive cell. The resistance of the photoconductive cell, which changes in relation to the amount of light striking it, forms part of a bridge circuit where the electrical output is indicative of the reflectance of the mirror surface. The output of the photoconductive bridge is amplified and directed to a thermoelectric element bonded to the base of the mirror. The thermoelectric element has two surfaces, one of which can be made cool by conducting heat through the other surface upon application of an electric current. The circuit is adjusted so that when the mirror is free of condensate, a maximum amount of cooling occurs. Then, as cooling takes place and condensate begins to form on the mirror, the cooling effect is proportionately decreased until equilibrium is attained. In case too much condensate is formed, the thermoelectric element can be employed to heat the mirror to return it to the equilibrium state and the dew point.

With most comminuted food compositions, when the determination is carried out in a laboratory or other space where the atmosphere above the food composition is maintained at substantially constant temperature, the method of determining the equilibrium dew point described above can be carried out within 10 minutes with great precision. The dew point at equilibrium and the ambient temperature as read on thermometer 7 (calibrated to 0.1° C.) are converted by means of standard tables to vapor pressures of water, from which the water activity of a food or other composition is calculated. The water activity, which is the effective concentration of water in a food or other composition, is the ratio of the partial pressure of water in a food (or other composition) to the vapor pressure of pure water at the same temperature. Expressed in equation form, $$Aw = [P/Po]_T$$

wherein Aw is the water activity, P equals the equilibrium vapor pressure of the water in a food as obtained from the equilibrium dew point of the atmosphere with which the food is in equilibrium and Po is the vapor pressure of pure water at the temperature of the ambient atmosphere with which the food is in equilibrium. Stated in another way, Aw = Relative Humidity of the Atmosphere in Equilibrium with a food/100

The following example describes the procedure for determining the water activity of a food in accordance with the method of the invention:

EXAMPLE

The calibration of the sensor 13 and the dew point hygrometer is carried out before a series of sample runs and possibly during such a series if any indication of deviation from normal operation becomes apparent. Such calibration is accomplished by placing a series of salt solution (or slurries) of well-known water activities within the system and checking the equilibrium dew point readings. For this purpose, a thick slurry of an analytic reagent grade salt, such as sodium chloride or zinc sulphate, in distilled de-ionized water is placed in the sample container and permitted to come to an equilibrium state. The water activity of saturated sodium chloride in water is known to be 0.75 at both 20° and 25° C. and the water activity of saturated zinc sulphate in water is known to be 0.90 at 20° C. and 0.88 at 25° C. (Rockland, L. B., Anal. Chem. 32, 1375 (1960) and Greenspan, L., Journal of Research of N.B.S.-A. Physics and Chemistry, 81A, No. 1, 89 (1977)).

When the sensor and dew point hygrometer have been calibrated, a food previously stored in a sample container, preferably in a comminuted state so as to speed up the attainment of equilibrium, is placed in the system. Each food sample is placed in a separate sample container, of approximately $4.73 \times 10^{-1}$ l. ($4.73 \times 10^{-4}$ m³) glass jar size such as a Mason jar, to a depth of about 2.54 cm. and stored therein with a cap on the jar for a minimum of about 4 hours (however, overnight may be more convenient) at the temperature at which the assay is to be made, e.g. 23.0±0.5° C. When all is in readiness for a determination of water activity to be made on a given sample, the cap is removed from a jar containing a sample and the jar is attached to the screw-on cap 4 of the apparatus described above. Circulation of the atmosphere, as described above, is begun. When it is apparent that equilibrium has been established in the system in accordance with the foregoing description of the operation of the apparatus, the ambient temperature reading (constant to within 0.1° C.) and, therefore, the temperature of the food is taken from 7 and is recorded for conversion to Po (see equation above). When the dew point reading on the hygrometer becomes constant, this is recorded for subsequent conversion to P to substitute in the equation above. These temperatures may be converted to water vapor pressures at the respective temperatures with the assistance of any acceptable table of vapor pressures of water below 100° C. Most handbooks of chemistry or physics provide such a table. For example, the CRC Handbook of Chemistry and Physics, 59th Edition (1978-79), published by CRC Press, Inc., West Palm Beach, Fla. 33409, at page D-232, contains such a table. Also, The American Institute of Physics Handbook, Third Edition (1972), published by McGraw-Hill Book Co. contains such a table at page 4–303ff. Also, the Smithsonian Meteorological Tables, Sixth Revised Edition (1951), published by The Smithsonian Institution, at page 350ff, contains such a table.

Table 1 gives results of water activity determinations for four foods using the apparatus of the invention and applying the method described above under Example:

Table 1

| Type of Food | Chocolate Nut Roll | Grated Parmesan Cheese | Quaker Oats | Tomato Paste |
|---|---|---|---|---|
| Dew Point, °C. | 19.8 | 18.0 | 10.0 | 21.8 |
| P, mm. Hg | 17.319 | 15.477 | 9.209 | 19.587 |
| Ambient temp., °C. | 22.0 | 22.8 | 23.0 | 23.0 |
| Po, mm. Hg | 19.827 | 20.815 | 21.068 | 21.068 |
| Aw | 0.87 | 0.74 | 0.44 | 0.93 |

The water activity of the food sample is the ratio of the vapor pressure of the atmosphere in equilibrium with the sample to the vapor pressure of pure water at the temperature of the sample (the same as the ambient temperature). In most cases when the food samples have been stored in closed containers in a constant temperature area at the temperature at which the assay is to be conducted, a single determination of water activity can be made within ten minutes. By having a large number of individual samples stored in jars for at least 4 hours in a constant temperature room, it is possible to carry out a large number of water activity determinations within a working day, each determination requiring about 10 minutes, or even less in the cases of some foods.

It is very important that the temperature of all parts of the apparatus as well as the sample being assayed be maintained as nearly constant as possible throughout the determination in order to obtain accurate water activity values. It is also important that no condensation of moisture occur within conduit 11 during a determination of water activity.

The present invention provides a distinct advantage over prior methods for determining the water activity of a water-containing composition in that the determination can usually be accomplished with great precision within ten minutes. This is a very small fraction of the time required for such determinations in accordance with prior art methods. One of the most important reasons for this difference is that in the past it has been customary for the sensor of a hygrometer being used in determining dew point to be located within the sample container and not to provide for circulation of the atmosphere above the food or other water-containing composition through a conduit and through a sensor located outside of the sample container, as in the present invention. Thus, the establishment of equilibrium was much slower in the prior art systems than in the system of the present invention.

It will be understood that various changes in the details, materials, and arrangements of parts which have been herein described and illustrated in order to explain the nature of the invention, may be made by those skilled in the art within the principle and scope of the invention.

We claim:

1. Apparatus for rapidly determining water activity of water-containing compositions within approximately ten minutes comprising, a closed container for holding a sample of a water-containing composition the water activity of which is to be determined; a closed conduit for conducting atmosphere from a first point in the interior of said closed container through a path exterior to said closed container and back into said closed container at a second point therein; a sensor means located in said closed conduit so that said atmosphere passes therethrough for sensing the condensation of moisture therein and the evaporation of moisture therefrom; an optically sensed, thermoelectrically cooled, condensation dew point hygrometer connected to said sensor means for detecting the dew point of said atmosphere; a substantially non-heat-generating pump means located in said closed conduit so that said atmosphere passes therethrough and is forced thereby to circulate through said closed container, said closed conduit, and said sensor means; means for determining the temperature of said water-containing composition and said atmosphere; and means for determining the dew point of said atmosphere as it passes through said sensor means at any selected time.

2. Apparatus according to claim 1, wherein said substantially non-heat-generating pump means is a diaphragm pump.

3. Apparatus according to claim 1, wherein said sensor means comprises a thermoelectrically cooled mirror surface upon which condensation of moisture from said atmosphere occurs and from which evaporation of moisture into said atmosphere occurs, the equilibrium of said condensation and said evaporation being detected by said optically sensed, thermoelectrically cooled, condensation dew point hygrometer and the temperature at which said equilibrium occurs being indicated by said dew point hygrometer as the dew point of said atmosphere.

4. Apparatus according to claim 1, wherein said means for determining the dew point of said atmosphere is a thermistor attached to or contained in said sensor means.

5. Method of rapidly determining the water activity of a water-containing composition in a closed space within approximately ten minutes, which comprises the steps of:
   a. continuously circulating the atmosphere above said water-containing composition in said closed space and through a conduit containing a sensor means for contacting said atmosphere and sensing the condensation of moisture thereon and the evaporation of moisture therefrom, said atmosphere being circulated through said conduit and back to said closed space by a substantially non-heat-generating pump means, said circulation of said atmosphere being continued until equilibrium is established at a substantially constant temperature;
   b. determining the dew point of said atmosphere at said equilibrium;
   c. determining the temperature of said atmosphere and, therefore, of said water-containing composition at said equilibrium; and
   d. calculating the water activity of said water-containing composition with the help of said dew point at equilibrium and the equilibrium vapor pressure of water at the temperature of said water-containing composition at equilibrium.

6. Method according to claim 5, wherein said substantially non-heat-generating pump means is a diaphragm pump.

7. Method according to claim 5, wherein said dew point is determined with an optically sensed, thermoelectrically cooled, condensation dew point hygrometer in combination with said sensor means.

8. Method according to claim 5, wherein said step of determining the temperature of said atmosphere and, therefore, of said water-containing composition at said equilibrium is carried out with a precision thermometer having the bulb thereof in said atmosphere in close proximity to said water-containing composition.

9. Method according to claim 6, wherein said dew point is determined with an optically sensed, thermoelectrically cooled, condensation dew point hygrometer in combination with said sensor means.

10. Method according to claim 9, wherein said step of determining the temperature of said atmosphere and, therefore, of said water-containing composition at said equilibrium is carried out with a precision thermometer having the bulb thereof in said atmosphere in close proximity to said water-containing composition.

* * * * *